United States Patent
Bittar et al.

(10) Patent No.: US 9,851,319 B2
(45) Date of Patent: Dec. 26, 2017

(54) NON-CONTACT FLUID RESISTIVITY MEASUREMENT

(71) Applicant: Halliburton Energy Services, Inc., Houston, TX (US)

(72) Inventors: Michael Bittar, Houston, TX (US); Jing Li, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 14/432,099

(22) PCT Filed: May 3, 2013

(86) PCT No.: PCT/US2013/039556
§ 371 (c)(1),
(2) Date: Mar. 27, 2015

(87) PCT Pub. No.: WO2014/178885
PCT Pub. Date: Nov. 6, 2014

(65) Prior Publication Data
US 2015/0260669 A1    Sep. 17, 2015

(51) Int. Cl.
*G01N 27/02*     (2006.01)
*G01V 3/10*      (2006.01)
(Continued)

(52) U.S. Cl.
CPC ........... *G01N 27/025* (2013.01); *E21B 49/08* (2013.01); *G01V 3/10* (2013.01); *G01V 3/107* (2013.01);
(Continued)

(58) Field of Classification Search
CPC ...... G01N 27/025; G01N 27/74; E21B 49/08; E21B 2049/085; G01V 3/10; G01V 3/107; G01V 3/18; G01V 3/28
(Continued)

(56) References Cited

U.S. PATENT DOCUMENTS 2,920,267 A * 1/1960 Miner .................... E21B 49/08
324/324
2,922,103 A * 1/1960 Smith ................... E21B 49/005
324/324
(Continued)

FOREIGN PATENT DOCUMENTS

EP     2253953 A1   11/2010
GB      936045 A    9/1963
WO   03/050529 A1   6/2003

OTHER PUBLICATIONS

G. E. Turner, "Liquid Metal Flow Measurement (Sodium) State-of-the-Art Study", Liquid Metal Engineering Center, Jun. 28, 1968, 76 pages.
(Continued)

*Primary Examiner* — Jermele M Hollington
*Assistant Examiner* — Christopher McAndrew
(74) *Attorney, Agent, or Firm* — Benjamin Fite; Baker Botts L.L.P.

(57) ABSTRACT

According to aspects of the present disclosure, systems and methods for measuring fluid resistivity are described herein. An example system may include a non-conductive tube. The non-conductive tube may be filled with a fluid, such as a formation fluid or drilling fluid, whose resistivity needs to be determined. A transmitter may be disposed around an outer surface of the non-conductive tube. A first receiver may be disposed around the outer surface of the non-conductive tube, and a second receiver may be positioned within a bore of the non-conductive tube. The transmitter may generate a primary electromagnetic field in a fluid within the tube, which may in turn generate an eddy current and a secondary electromagnetic field. The first and second receivers may be used to identify the eddy current and the resistivity of the fluid.

12 Claims, 6 Drawing Sheets

(51) Int. Cl.
*G01V 3/18* (2006.01)
*G01V 3/28* (2006.01)
*G01N 27/74* (2006.01)
*E21B 49/08* (2006.01)

(52) U.S. Cl.
CPC .................. *G01V 3/18* (2013.01); *G01V 3/28* (2013.01); *E21B 2049/085* (2013.01); *G01N 27/74* (2013.01)

(58) Field of Classification Search
USPC ........................................................ 324/324
See application file for complete search history.

(56) References Cited

U.S. PATENT DOCUMENTS

| | | | | |
|---|---|---|---|---|
| 3,030,573 | A * | 4/1962 | Yamashita | G01N 27/025 324/445 |
| 3,327,203 | A | 6/1967 | Georges | |
| 3,493,850 | A * | 2/1970 | Schuster | G01V 3/26 324/342 |
| 3,688,187 | A * | 8/1972 | Loos | G01D 5/202 324/224 |
| 3,821,894 | A * | 7/1974 | Roeben | B63B 59/04 73/170.29 |
| 4,897,605 | A | 1/1990 | Cox et al. | |
| 5,442,294 | A | 8/1995 | Rorden et al. | |
| 5,892,362 | A | 4/1999 | Warren et al. | |
| 7,624,794 | B2 * | 12/2009 | Freedman | E21B 49/08 166/264 |
| 2004/0085077 | A1 * | 5/2004 | Nyfors | G01N 22/00 324/637 |
| 2005/0030034 | A1 * | 2/2005 | Ganesan | E21B 49/10 324/324 |
| 2005/0246151 | A1 * | 11/2005 | DiFoggio | G01V 1/50 703/10 |
| 2006/0005965 | A1 * | 1/2006 | Chouzenoux | E21B 47/0006 166/250.11 |
| 2008/0035332 | A1 * | 2/2008 | Freedman | E21B 49/08 166/250.01 |
| 2008/0204013 | A1 * | 8/2008 | Badry | G01N 24/081 324/303 |
| 2009/0085583 | A1 * | 4/2009 | Waid | G01N 27/221 324/663 |
| 2009/0267617 | A1 * | 10/2009 | Seyfi | G01N 27/023 324/655 |
| 2009/0322338 | A1 * | 12/2009 | Godefroy | G01V 3/24 324/355 |
| 2011/0031972 | A1 * | 2/2011 | Pelletier | E21B 47/102 324/324 |
| 2011/0037462 | A1 | 2/2011 | Bosnar et al. | |
| 2011/0071762 | A1 | 3/2011 | Hagiwara et al. | |
| 2011/0184711 | A1 * | 7/2011 | Altman | E21B 49/005 703/10 |
| 2011/0251795 | A1 * | 10/2011 | DiFoggio | E21B 49/10 702/11 |
| 2013/0021042 | A1 | 1/2013 | Laemmel et al. | |
| 2013/0340518 | A1 * | 12/2013 | Jones | E21B 49/005 73/152.55 |

OTHER PUBLICATIONS

Bonner et al., "Resistivity While Drilling—Images from the string", Oilfield Review, Spring 1996, 61 pages.
International Search Report and Written Opinion issued in related PCT Application No. PCT/US213/039556 dated Apr. 24, 2014, 16 pages.

* cited by examiner

NON-CONTACT FLUID RESISTIVITY MEASUREMENT

CROSS-REFERENCE TO RELATED APPLICATION

The present application is a U.S. National Stage Application of International Application No. PCT/US2013/039556 filed May 3, 2013, which is incorporated herein by reference in its entirety for all purposes.

BACKGROUND

The present disclosure relates generally to well drilling operations and, more particularly, to non-contact fluid resistivity measurement.

Determining the resistivity of downhole fluid can be important for a variety of reasons. For example, determining the resistivity of fluid extracted from the formation may identify if the correct formation strata has been identified, and if the formation will effectively produce hydrocarbons. In another example, drilling fluids used to drill a borehole may be tested to determine if the formulation is correct for the subterranean conditions within the borehole. Existing resistivity measurement tools suffer from various mechanical and electrical problems, including, but not limited to, ineffective sealing, problems generating current within the fluid for testing purposes, and problems separating electromagnetic ("EM") fields for measurement purposes.

FIGURES

Some specific exemplary embodiments of the disclosure may be understood by referring, in part, to the following description and the accompanying drawings.

FIGS. 5A and 5B are graphs illustrating example sensor responses, according to aspects of the present disclosure While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to well drilling operations and, more particularly, to systems and methods for non-contact fluid resistivity measurement.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass, or otherwise nonlinear wellbores in any type of subterranean formation. Embodiments may be applicable to injection wells, and production wells, including natural resource production wells such as hydrogen sulfide, hydrocarbons or geothermal wells; as well as borehole construction for river crossing tunneling and other such tunneling boreholes for near surface construction purposes or borehole u-tube pipelines used for the transportation of fluids such as hydrocarbons. Embodiments described below with respect to one implementation are not intended to be limiting.

According to aspects of the present disclosure, systems and methods for measuring fluid resistivity are described herein. An example system may include a non-conductive tube. The non-conductive tube may be filled with a fluid, such as a formation fluid or drilling fluid, whose resistivity needs to be determined. A transmitter may be disposed around an outer surface of the non-conductive tube. A first receiver may be disposed around the outer surface of the non-conductive tube, and a second receiver may be positioned within a bore of the non-conductive tube. The transmitter may generate a primary electromagnetic field in a fluid within the tube, which may in turn generate an eddy current and a secondary electromagnetic field. The first and second receivers may be used to identify the eddy current and the resistivity of the fluid.

Figure 1A:
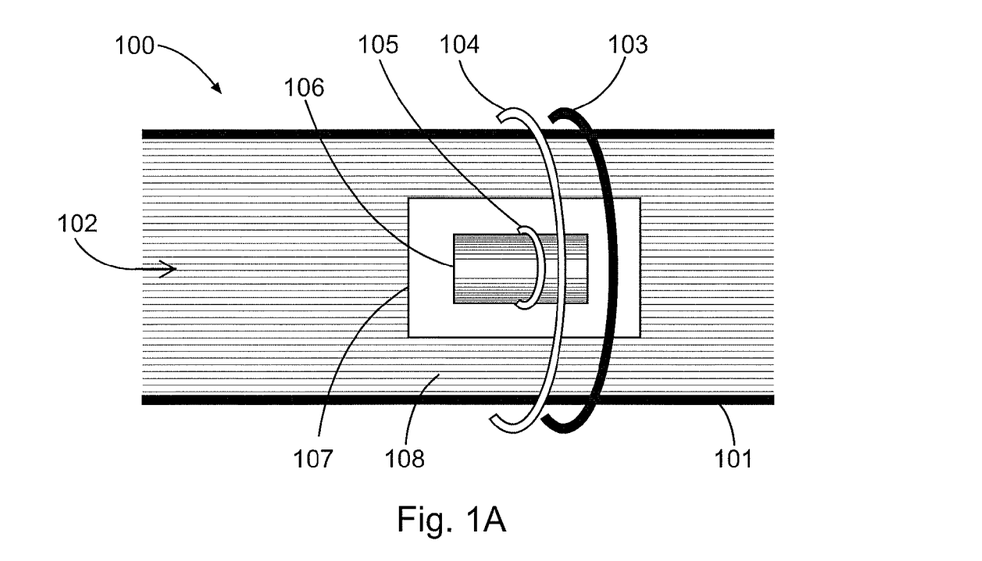
FIGS. 1A and 1B are diagrams illustrating an example sensor, according to aspects of the present disclosure.

FIG. 1 is a diagram illustrating an example sensor 100, according to aspects of the present disclosure. The sensor 100 may be a fluid resistivity sensor, and in certain embodiments, may be located at the surface to identify the resistivity of a fluid captured within a borehole and transported to the surface. In other embodiments, the sensor 100 may be located within the borehole, including, but not limited to, being incorporated into a logging-while-drilling (LWD) or measuring-while-drilling (MWD) portion of a drilling assembly. The sensor 100 may also be located in a downhole wireline tool. Other configurations are possible, as would be appreciated by one of ordinary skill in the art in view of this disclosure.

The sensor 100 may comprise a non-conductive tube 101. The non-conductive tube 101 may be characterized by its composition from a material that does not conduct electricity, such as plastic, polymer, glass, etc. The non-conductive tube 101 may receive a fluid 102, and may measure the resistivity of the fluid 102, as will be described below. In certain embodiments, the fluid 102 may comprise a fluid sample from a subterranean formation or a drilling fluid sample that is introduced into the non-conductive tube 101. Introducing the fluid 102 into the non-conductive tube 101 may include allowing the fluid 102 to enter the pipe, either by placing the non-conductive tube 101 in fluid communication with a fluid source, or by selectively allowing fluid 102 into the non-conductive tube 101 through a valve system. The non-conductive tube 101 may be selectively in fluid communication with the formation or with an annulus between a drilling assembly and a borehole, to receive the fluid 102.

A transmitter 103 may be disposed around an outer surface of the non-conductive tube 101. A first receiver 104 may be disposed around the outer surface of the non-conductive tube 101, adjacent to the transmitter 103. Additionally, a second receiver 105 may be positioned within a bore 108 of the non-conductive tube 101. In certain embodiments, the transmitter 103, the first receiver 104, and the second receiver 105 may comprise separate coil antennas. The transmitter 103 and first receiver 104 may be coil or loop antennas that are wrapped around the non-conductive tube 101, the number of corresponding loops being selected to optimize the reception of magnetic fields within the non-conductive housing 101 that will be described below.

In certain embodiments, the second receiver 105 may comprise a coil or loop antenna that is wrapped around a core 106 and that is coaxial with the first receiver 104. Additionally, the first receiver 104 and the second receiver 105 may be positioned at the same location along the length of the non-conductive tube 101. The core 106 may be composed of a material with low electrical conductivity, such as ferrimagnetic ceramic compounds derived from iron oxides such as hematite or magnetite as well as oxides of other metals, or a non-conductive material. As can be seen, the core 106 may be positioned within the bore 108 of the non-conductive tube 101. In certain embodiments, the core 106 and second receiver 105 may be at least partially disposed in a non-conductive housing 107 that is also positioned within the bore 108 of the non-conductive tube 101. The non-conductive housing 107 may be characterized by its composition from a material that does not conduct electricity, such as plastic, polymer, glass, etc. The non-conductive housing 107 may be sealed to prevent fluid 102 from contacting the second receiver 105. Contact between fluid 102 and second receiver 105 may cause the second receiver 105 to erode, decreasing the useful life of the sensor 100.

Figure 1B:
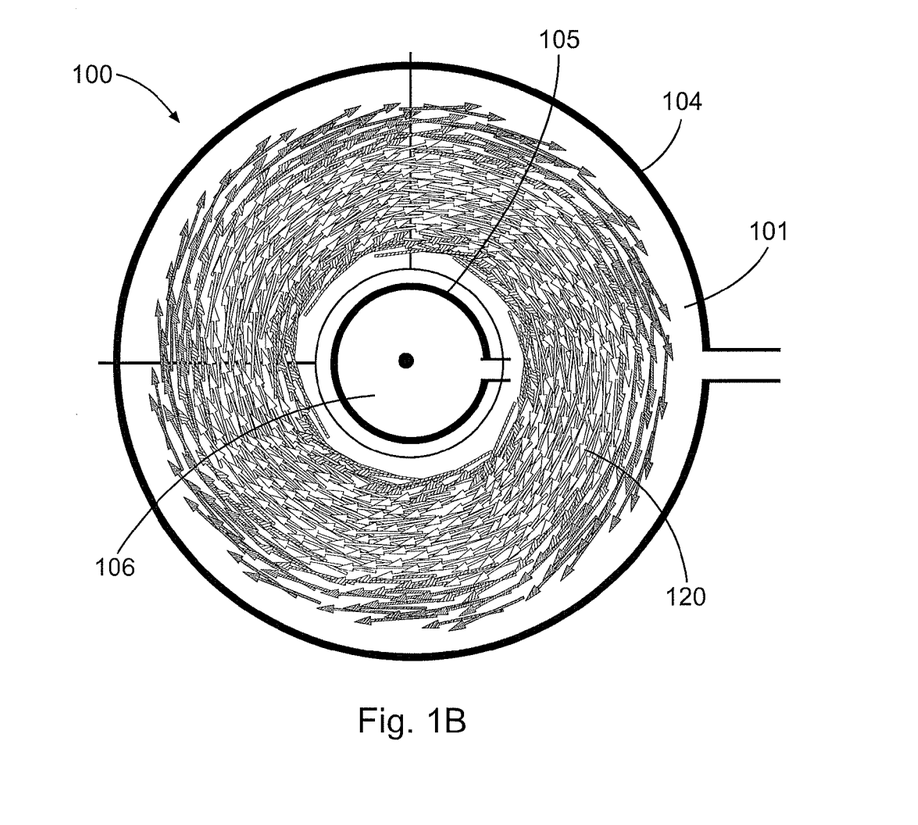

In operation, the transmitter 103 may generate a primary electromagnetic ("EM") field within the non-conductive tube 101 and the fluid 102 disposed within the non-conductive tube 101. Specifically, the transmitter 103 may be coupled to a current source (not shown) that drives a current through the transmitter 103 to generate the primary EM field. The primary EM field may cause an eddy current 120 within the fluid 102. FIG. 1B illustrates an example eddy current 120 within the fluid 102. The eddy current 120 may generate a secondary EM field within the fluid 102. The primary EM field and the secondary EM field may be received at the first receiver 104 and the second receiver 105.

The outputs of the first receiver 104 and second receiver 105 may be used to determine the eddy current 120 and a resistivity of the fluid 102. In certain embodiments, the first receiver 104 and the second receiver 105 may receive the primary EM field, and the received primary EM field at the first receiver 104 may be proportional to the received primary EM field at the second receiver 105. Additionally, the first receiver 104 and the second receiver 105 may receive the secondary EM field, and the received secondary EM field at the first receiver 104 may not be proportional to the received secondary EM field at the second receiver 105. Specifically, the received secondary EM field at the second receiver 105 may be much larger than the received secondary EM field at the first receiver 104.

In certain embodiments, the output of the second receiver 105 may be increased such that the received primary EM field at the second receiver is approximately equivalent to the received primary EM field at the first sensor 104. For example, the second receiver 105 may be coupled to an amplification circuit, to boost the strength of the output of the second receiver 105. In a second example, the first receiver 104 and the second receiver 105 may comprise coil or loop antenna that are configured through the corresponding number of loops such that the received primary EM field at the second receiver 105 is approximately equivalent to the receiver primary EM field at the first receiver 104. The outputs of the first receiver 104 and the second receiver 105 can then be combined to cancel the received primary EM field from the outputs of the first receiver 104 and the second receiver 105. The remainder may comprise the received secondary EM field, which can be used to calculate the eddy current 120 and the resistivity of the fluid 102.

Figure 2A:
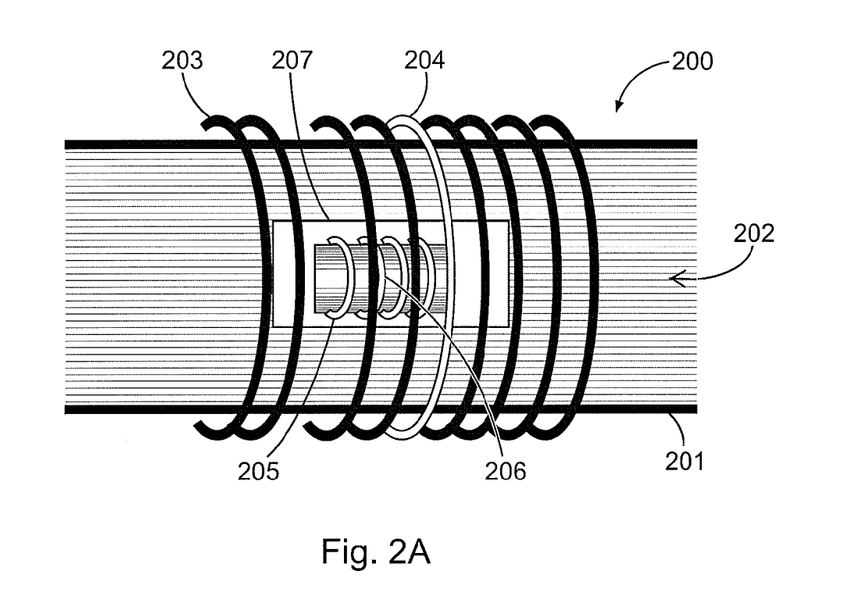
FIGS. 2A and 2B are diagrams illustrating an example sensor, according to aspects of the present disclosure.
Figure 2B:
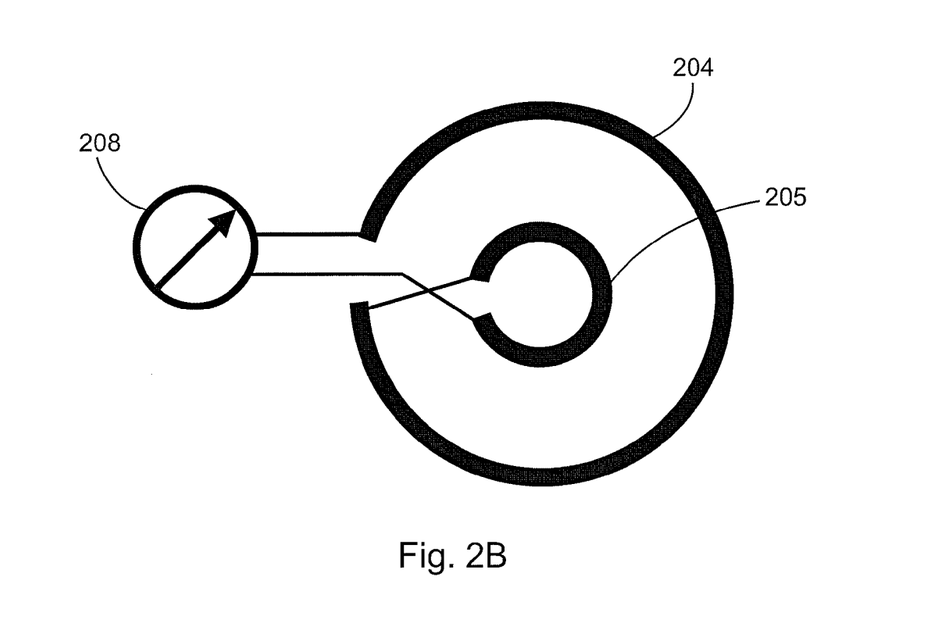

FIGS. 2A and 2B are diagrams illustrating another example sensor 200, according to aspects of the present disclosure. As can be seen, the sensor 200 may comprise a non-conductive tube 201 filled with fluid 202, and around which a transmitter 203 and a first receiver 204 are disposed. A second receiver 205 may be disposed within the non-conductive tube 201, wrapped around a coil 206, both of which are at least partially disposed within a non-conductive housing 207. Like in sensor 100, the transmitter 203 may generate a primary EM field within the non-conductive tube 201 and the fluid 202 within the non-conductive tube 201. The primary EM field may cause an eddy current within the fluid 202 that generates a secondary EM field.

As can be seen, each of the transmitter 203, the first receiver 204, and the second receiver 205 may comprise separate coil antennas. As can also be seen, each of the coil antennas may have a different number of loops. For example, the transmitter 203 may comprise a first coil antenna with two loops around non-conductive tube 201, and first receiver 204 may comprise a second coil antenna with seven loops around non-conductive loop 201. Likewise, second receiver 205 may comprise a third coil antenna with four loops around coil 206. In certain embodiments, the loops of the second and third coil antenna may be optimized such that the received primary EM field at the second receiver 205 is approximately the same strength as the received primary EM field at the first receiver 204, with the outputs of the first receiver 204 and the second receiver 205 combined to cancel the primary EM field. The loops of the second and third coil may be optimized to minimize the combined output when air fills the non-conductive tube 201.

FIG. 2B is a diagram illustrating an example configuration of the sensor 200 to cancel the primary EM field. Specifically, the first receiver 204 may be cross connected to the second receiver 205 such that the current generated in both have opposite polarities. The primary EM field and secondary EM field may cause a first current to be generated on the first receiver 204 and a second current to be generated on the second receiver 205. By cross-connecting the first receiver 204 and the second receiver 205, the first and second currents may flow in opposite directions, and the combined output at the circuitry 208 may therefore be the difference between the first and second currents. The combined output may correspond to the eddy current, through which a resistivity value of the fluid 202 may be calculated.

Figure 3A:
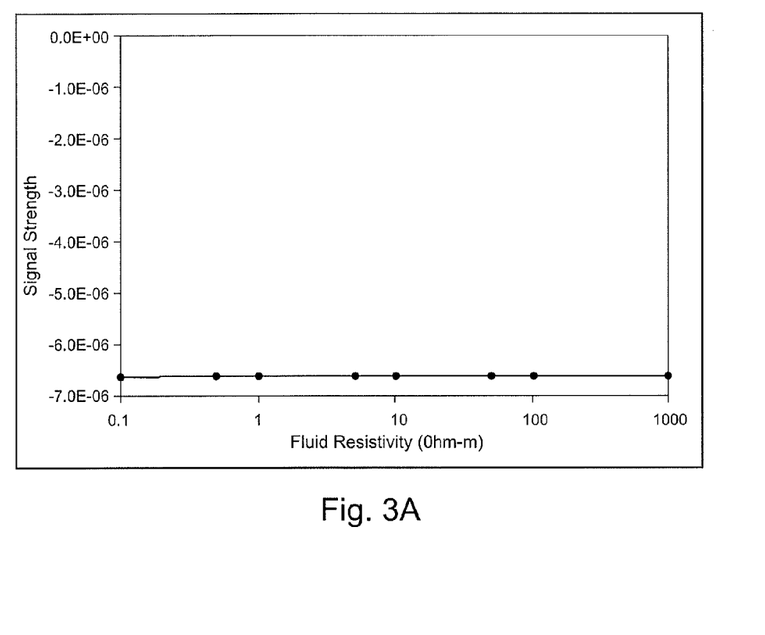
FIGS. 3A and 3B are graphs illustrating example sensor responses, according to aspects of the present disclosure.
Figure 3B:
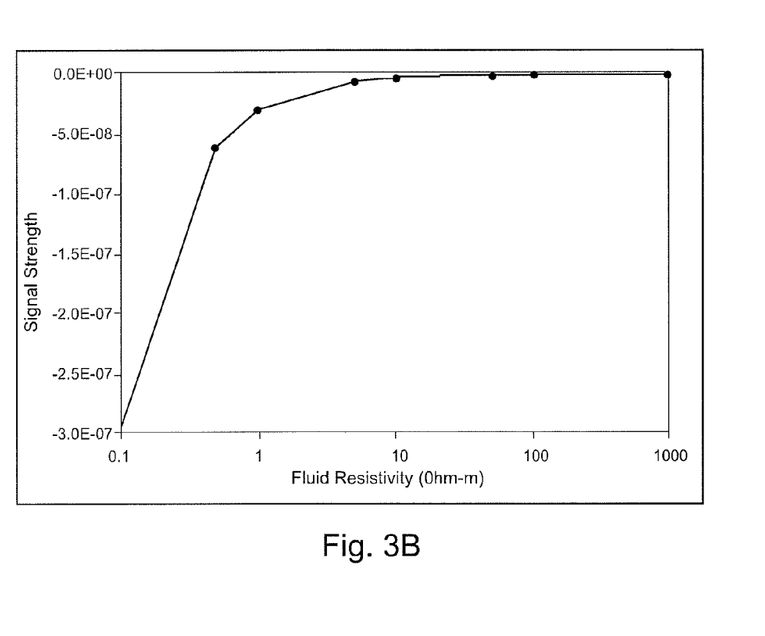

FIG. 3A is a graph illustrating an example response from a second receiver, similar to second receivers 105 and 205, in the presence of a primary EM field. The graph in FIG. 3A plots a signal strength of the primary EM field versus the resistivity of the fluid within a non-conductive tube. As can be seen, the signal strength is almost uniformly reduced at the second receiver, with a slight variation when the fluid resistivity is low. FIG. 3B, in contrast, is a graph illustrating the signal strength of the combined outputs of first and second receivers, similar to those described above. Specifically, FIG. 3B illustrates the strength of the total received secondary EM field, with the outputs of the first receiver and second receiver combining to cancel the primary EM field.

Figure 4A:
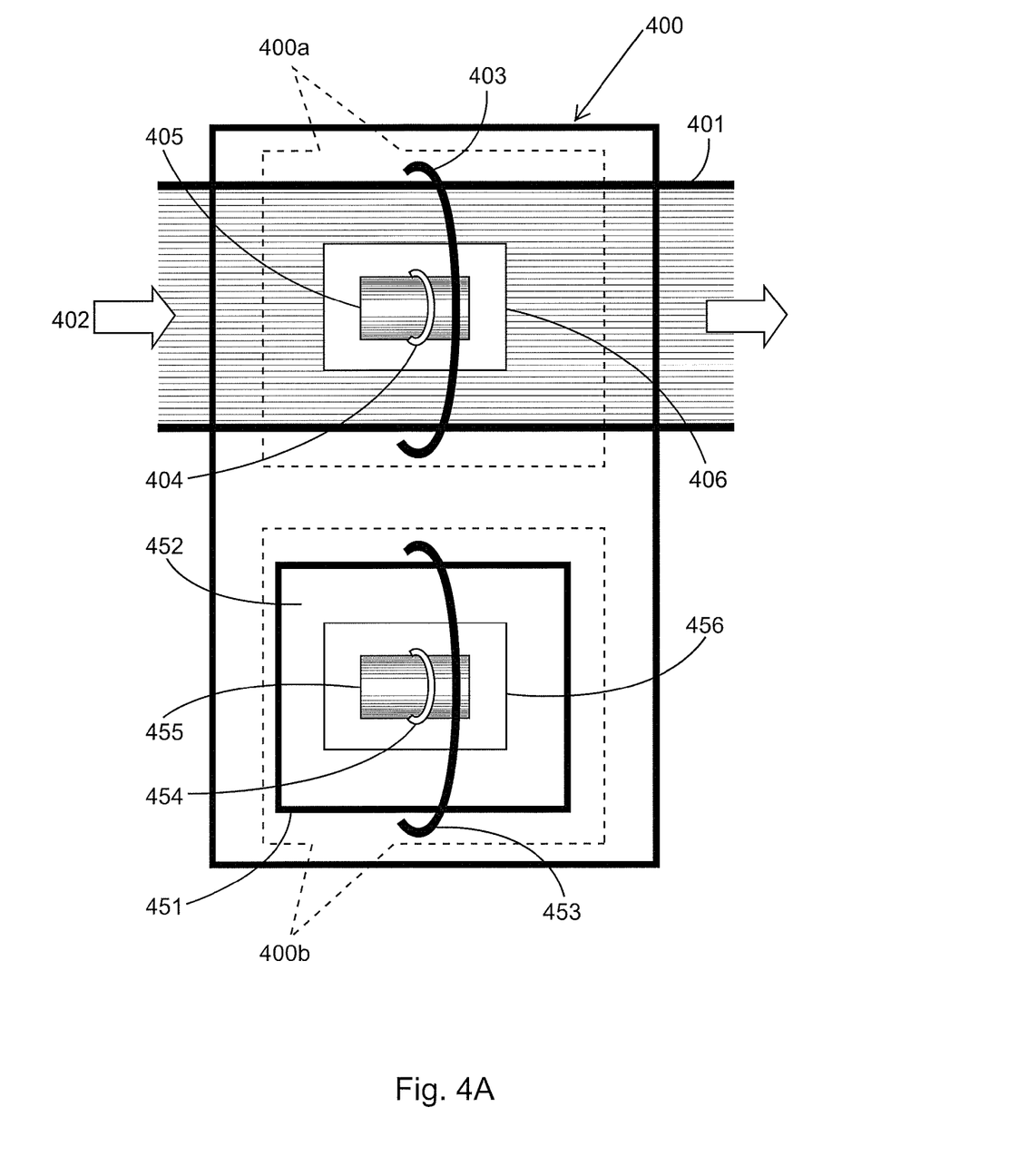
FIGS. 4A, 4B, and 4C are diagrams illustrating an example sensor, according to aspects of the present disclosure.
Figure 4B:
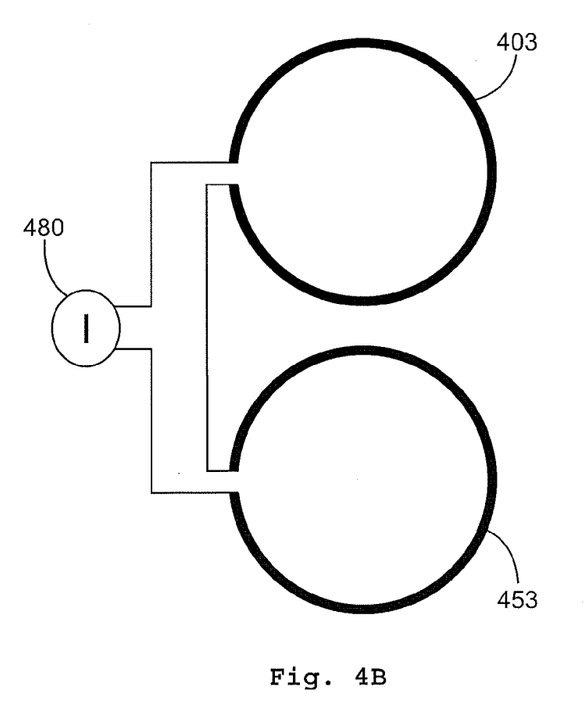
Figure 4C:
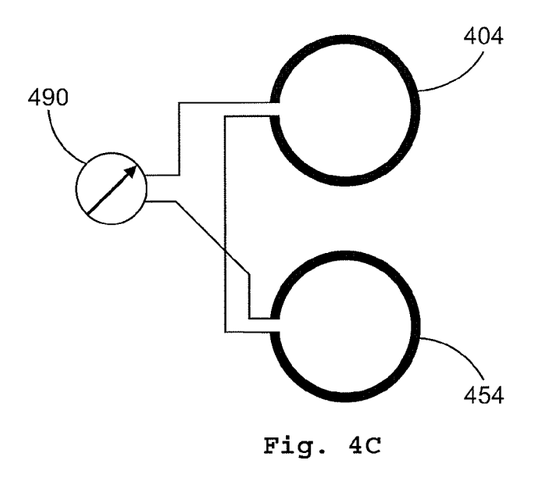

FIGS. 4A-C are diagrams illustrating an example sensor configuration, according to aspects of the present disclosure. As will be described below, the sensor 400 may differ from the sensors described above by using a reference sensor 400b to cancel the primary EM field within a main sensor 400a. As can be seen, the main sensor 400a may comprise a first non-conductive tube 401 filled with fluid 402, and around which a first transmitter 403 is disposed. A first receiver 404 may be disposed within the first non-conductive tube 401, wrapped around a first core 405, both of which being at least partially disposed within a first non-conductive housing 406. The first transmitter 403 may generate a primary EM field within the first non-conductive tube 401 and the fluid 402 within the first non-conductive tube 401. The primary EM field may cause an eddy current within the fluid 402 that generates a secondary EM field.

The reference sensor 400b may comprise a second non-conductive tube 451 that is sealed and filled with fluid 452 of known resistivity, such as air. A second transmitter 453 may be disposed around the second non-conductive tube 451. A second receiver 454 may be disposed within the second non-conductive tube 451, wrapped around a second core 455, both of which being at least partially disposed within a second non-conductive housing 456. The transmitter 453 may generate a primary EM field within the second non-conductive tube 451 and the fluid 452 within the second non-conductive tube 401.

As can be seen in FIG. 4B, the first transmitter 403 and the second transmitter 453 may be connected in series to a current source 480. The current source 480 may generate the same primary EM field in both the first non-conductive tube 401 and the second non-conductive tube 402. The primary EM field may generate an eddy current within fluid 402 in the first non-conductive tube 401, which may in turn generate a secondary EM field within the first non-conductive tube 401. In certain instances, such as where the second non-conductive tube 451 is filled with air, the primary EM field may not generate an eddy current or a secondary EM field. In other instances, such as where the second non-conductive tube 451 is filled with a fluid of known resistivity, the primary EM field may generate an eddy current and secondary EM field with known values.

Because the secondary EM field in the second non-conductive tube 451 is either known or not present, the output of the second receiver 454 may be treated as a reference, and used to cancel the primary EM field component within the output of the first receiver 404. For example, as can be seen in FIG. 4C the first receiver 404 may be cross-connected to the second receiver 454, with their combined output sensed at electrical component 490. The primary EM field in both the first non-conductive tube 401 and the second non-conductive tube 451 may be substantially the same, such that the cross connection of the receivers 404 and 454 may cancel out the corresponding primary EM field component and leave only the current generated by the secondary EM field at the components 490.

Figure 5A:
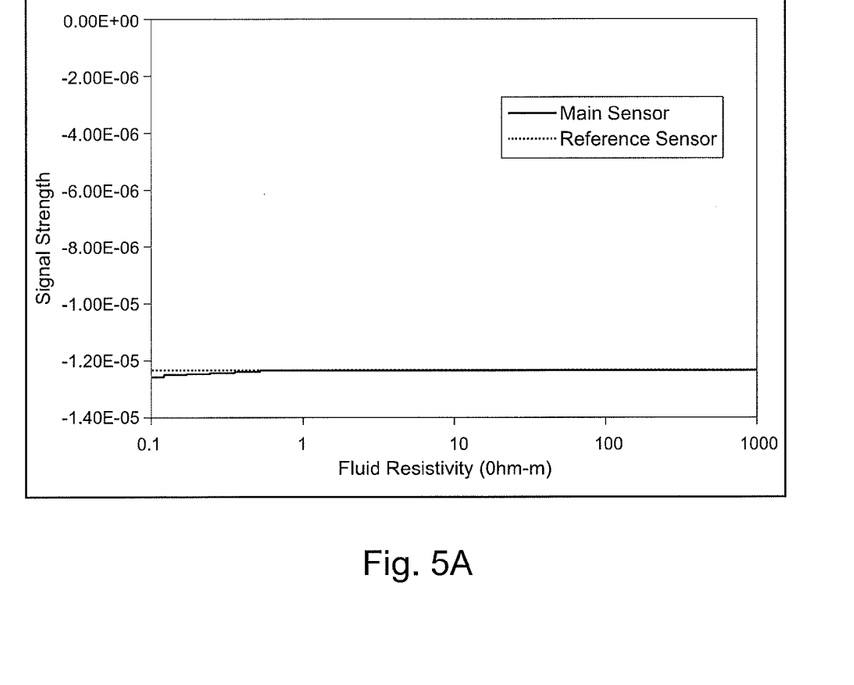
Figure 5B:
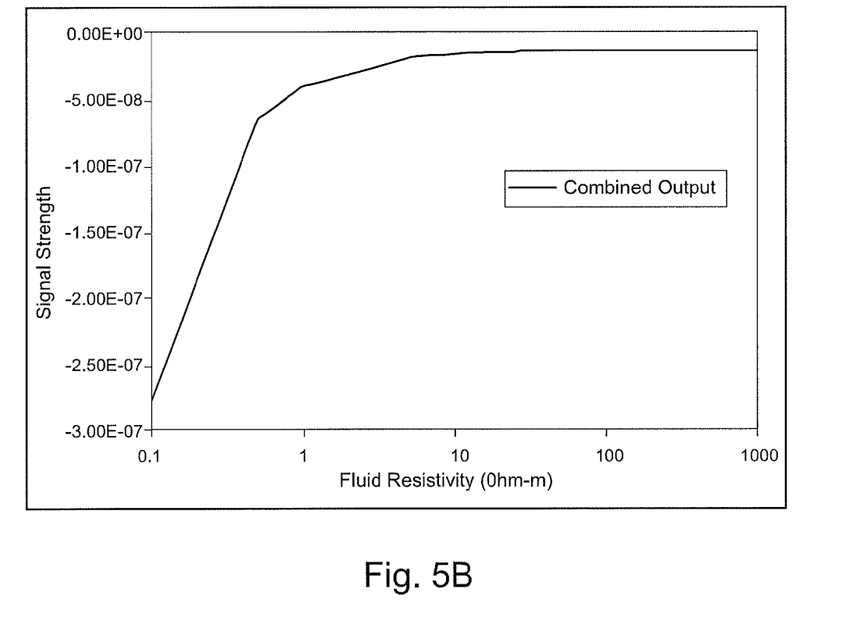

FIG. 5A is a graph illustrating an example response from first receiver 404 and second receiver 454, in the presence of a primary EM field. The graph in FIG. 5A plots a signal strength of the primary EM field versus the resistivity of the fluid within a non-conductive tube. As can be seen, the signal strength is essentially uniform in the reference sensor, but shows a dip in the main sensor, with a slight variation when the fluid resistivity is low. FIG. 5B, in contrast, is a graph illustrating the signal strength of the combined outputs of first receiver 404 and second receiver 454. Specifically, FIG. 5B illustrates the strength of the total received secondary EM field, with the outputs of the first receiver and second receiver combining to cancel the primary EM field.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces. Additionally, the terms "couple" or "coupled" or any common variation as used in the detailed description or claims are not intended to be limited to a direct coupling. Rather two elements may be coupled indirectly and still be considered coupled within the scope of the detailed description and claims.

What is claimed is:

1. A method for measuring fluid resistivity, comprising:
   introducing a first fluid into a first non-conductive tube;
   introducing a second fluid into a second non-conductive tube, wherein the second non-conductive tube is sealed;
   generating a first electromagnetic field within the first non-conductive tube and the first fluid with a first transmitter disposed around an outer surface of the first non-conductive tube, wherein the first electromagnetic field causes a first eddy current within the first fluid, and the first eddy current generates a first secondary electromagnetic field;
   receiving at a first receiver positioned within a bore of the first non-conductive tube the first electromagnetic field and the first secondary electromagnetic field at a first receiver disposed around the outer surface of the first non-conductive tube;
   generating a second secondary electromagnetic field within the second non-conductive tube and the second fluid with a second transmitter disposed around an outer surface of the second non-conductive tube, wherein the first transmitter and the second transmitter are connected in series;
   receiving the first electromagnetic field and the first secondary electromagnetic field at a second receiver positioned within a bore of the second non-conductive tube, wherein the first receiver is connected to the second receiver; and
   calculating a resistivity value of the second fluid based, at least in part, on a combined output from a circuitry coupled between the first receiver and the second receiver, wherein the combined output corresponds to an eddy current generated by the first secondary electromagnetic field within the first fluid and the second secondary electromagnetic field within the second fluid detected at the circuitry.

2. The method of claim 1, wherein the first receiver is at least partially disposed within a first non-conductive housing within the bore of the first non-conductive tube, and wherein the second receiver is at least partially disposed within a second non-conductive housing within the bore of the second non-conductive tube.

3. The method of claim 2, wherein the first receiver is disposed around a first core positioned within the first non-conductive housing, and the second receiver is disposed around a second core positioned within the second non-conductive housing.

4. The method of claim 1, wherein the first transmitter, the second transmitter, the first receiver, and the second receiver comprise coil antennas.

5. The method of claim 3, wherein:
the first receiver comprises a first coil antenna with a plurality of turns around the first non-conductive tube; and
the second receiver comprises a second coil antenna with a plurality of turns around the second core positioned within the second non-conductive housing.

6. The method of claim 1, further comprising determining the secondary electromagnetic field using an output of the first receiver and an output of the second receiver.

7. A system for measuring fluid resistivity, comprising:
a first non-conductive tube;
a second non-conductive tube, wherein the second non-conductive tube is sealed;
a first transmitter disposed around an outer surface of the first non-conductive tube;
a first fluid disposed within the first non-conductive tube, wherein the first transmitter generates a first electromagnetic field within the first non-conductive tube and the first fluid, wherein the first electromagnetic field causes a first eddy current within the first fluid that generates a first secondary electromagnetic field;
a second transmitter disposed around an outer surface of the second non-conductive tube, wherein the first transmitter and the second transmitter are connected in series;
a second fluid disposed within the second non-conductive tube, wherein the second transmitter generates a second secondary electromagnetic field within the second non-conductive tube and the second fluid;
a first receiver positioned within a bore of the first non-conductive tube;
a second receiver positioned within a bore of the second non-conductive tube, wherein the first receiver is connected to the second receiver; and
an electrical component coupled between the first receiver and the second receiver, wherein a combined output of the electrical component is associated with a resistivity value of the second fluid, wherein the combined output corresponds to an eddy current generated by the first secondary electromagnetic field within the first fluid and the second secondary electromagnetic field within the second fluid and detected at the electrical component.

8. The system of claim 7, wherein the first transmitter, the second transmitter, the first receiver, and the second receiver comprise coil antenna.

9. The system of claim 8, wherein the second non-conductive tube is sealed and filled with a fluid of known resistivity.

10. The system of claim 9, wherein the first transmitter and the second transmitter are connected in series with a current source.

11. The system of claim 7, further comprising:
a first non-conductive housing positioned within the bore of the first non-conducive tube, wherein the first receiver is at least partially disposed within the first non-conductive housing; and
a second non-conductive housing positioned within the bore of the second non-conducive tube, wherein the second receiver is at least partially disposed within the second non-conductive housing.

12. The system of claim 11, wherein:
the first receiver is disposed around a first core positioned within the first non-conductive housing
the second receiver is disposed around a second core positioned within the second non-conductive housing.

* * * * *